United States Patent
Grandi et al.

(10) Patent No.: US 9,855,325 B2
(45) Date of Patent: Jan. 2, 2018

(54) IMMUNOGENIC COMPOSITION

(71) Applicant: GlaxoSmithKline Biologicals SA, Rixensart (BE)

(72) Inventors: Guido Grandi, Segrate (IT); Immaculada Margarit Y Ros, Siena (IT); Domenico Maione, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/424,370

(22) PCT Filed: Oct. 3, 2013

(86) PCT No.: PCT/EP2013/070656
§ 371 (c)(1),
(2) Date: Feb. 26, 2015

(87) PCT Pub. No.: WO2014/053612
PCT Pub. Date: Apr. 10, 2014

(65) Prior Publication Data
US 2015/0224204 A1    Aug. 13, 2015

Related U.S. Application Data

(60) Provisional application No. 61/744,880, filed on Oct. 3, 2012, provisional application No. 61/799,123, filed on Mar. 15, 2013.

(51) Int. Cl.

| | |
|---|---|
| *A61K 39/09* | (2006.01) |
| *A61K 39/00* | (2006.01) |
| *A61K 39/05* | (2006.01) |
| *A61K 39/08* | (2006.01) |
| *A61K 39/02* | (2006.01) |
| *A61K 39/13* | (2006.01) |
| *A61K 39/12* | (2006.01) |
| *C12N 7/00* | (2006.01) |
| *A61K 9/00* | (2006.01) |
| *A61K 47/64* | (2017.01) |

(52) U.S. Cl.
CPC .......... *A61K 39/092* (2013.01); *A61K 9/0019* (2013.01); *A61K 39/0018* (2013.01); *A61K 39/05* (2013.01); *A61K 39/08* (2013.01); *A61K 39/099* (2013.01); *A61K 39/12* (2013.01); *A61K 39/13* (2013.01); *A61K 47/646* (2017.08); *C12N 7/00* (2013.01); *A61K 2039/55* (2013.01); *A61K 2039/55505* (2013.01); *A61K 2039/6037* (2013.01); *A61K 2039/70* (2013.01); *C12N 2770/32334* (2013.01); *C12N 2770/32634* (2013.01)

(58) Field of Classification Search
None
See application file for complete search history.

(56) References Cited

U.S. PATENT DOCUMENTS

2009/0043077 A1 *  2/2009 Berti ...................... A61K 39/09
                                                             530/363

FOREIGN PATENT DOCUMENTS

IT    WO 2012035519 A1 *  3/2012  ........... A61K 39/092

OTHER PUBLICATIONS

Baker, et al., Safety and immunogenicity of a bivalent group B streptococcal conjugate vaccine for serotypes II nd III, J Infect Dis 188(1): 66-73 (2003).
Edwards, Morven S., Group B streptococcal conjugate vaccine A timely concept for which the time has come, Human Vaccines 4(6): 444-448 (2008).

* cited by examiner

*Primary Examiner* — Brian Gangle
(74) *Attorney, Agent, or Firm* — Virginia G. Campen

(57) ABSTRACT

The invention provides an immunogenic composition comprising: a) a conjugate that is a capsular saccharide from GBS serotype Ia conjugated to a carrier protein; b) a conjugate that is a capsular saccharide from GBS serotype Ib conjugated to a carrier protein; c) a conjugate that is a capsular saccharide from GBS serotype III conjugated to a carrier protein; d) a conjugate that is a capsular saccharide from GBS serotype II conjugated to a carrier protein; and e) a conjugate that is a capsular saccharide from GBS serotype V conjugated to a carrier protein.

18 Claims, 10 Drawing Sheets

IMMUNOGENIC COMPOSITION

RELATED APPLICATIONS

This application is the U.S. National Phase of International Application No. PCT/EP2013/070656, entitled "IMMUNOGENIC COMPOSITIONS," filed Oct. 3, 2013 and published in English, which claims the benefit of U.S. provisional application 61/744,880 filed Oct. 3, 2012 and US provisional application 61/799,123 filed Mar. 15 2013, the complete contents of all of which are hereby incorporated herein by reference for all purposes.

TECHNICAL FIELD

This invention is in the field of immunogenic compositions comprising conjugates of *Streptococcus agalactiae* capsular saccharides and carrier proteins. The compositions are useful for immunisation.

BACKGROUND ART

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of Vaccines (2004) eds. Plotkin & Orenstein. ISBN 0-7216-9688-0].

Another bacterium for which conjugate vaccines have been described is *Streptococcus agalactiae*, also known as 'group B *streptococcus*', or simply as 'GBS'. Much of this work has been performed by Dennis Kasper and colleagues, and is described in documents such as references 1 to 9. Conjugate vaccines for each of GBS serotypes Ia, Ib, II, III, and V have been shown to be safe and immunogenic in humans [10& 11]. However, there remains a need for further and improved GBS conjugate vaccines.

DISCLOSURE OF THE INVENTION

The invention provides an immunogenic composition comprising: i) a capsular saccharide from GBS serotype Ia conjugated to a carrier protein; ii) a capsular saccharide from GBS serotype Ib conjugated to a carrier protein; iii) a capsular saccharide from GBS serotype III conjugated to a carrier protein; iv) a capsular saccharide from GBS serotype V conjugated to a carrier protein; and v) a capsular saccharide from GBS serotype II conjugated to a carrier protein.

Typically, the immunogenic composition will not comprise any conjugates other than those specifically mentioned, particularly conjugates comprising capsular saccharides from GBS serotypes other than those specifically mentioned. However, in some embodiments, the compositions may comprise other conjugates, including conjugates comprising capsular saccharides from other GBS serotypes. For example, the compositions may comprise a conjugate that is a capsular saccharide from GBS serotype VI conjugated to a carrier protein. In another possibility, the compositions may comprise a conjugate that is a capsular saccharide from GBS serotype VIII conjugated to a carrier protein.

The immunogenic compositions described above may comprise any suitable amount of the capsular saccharide(s) per unit dose. Suitable amounts of the capsular saccharide(s) may be from 0.1 to 50 μg per unit dose. Typically each GBS capsular saccharide is present at an amount from 1 to 30 μg, for example from 2 to 25 μg, and in particular from 5 to 20 μg. Suitable amounts of the capsular saccharide(s) may include 5, 10 and 20 μg per unit dose.

It may be possible to further minimise the amount of capsular saccharide(s) per unit dose. In particular, suitable amounts of the capsular saccharide(s) may be from 0.1 to 5 μg per unit dose. Typically, each GBS capsular saccharide may therefore be present at an amount from 0.1 to 5 μg, e.g. 0.5, 2.5 or 5 μg, per unit dose. For example, each GBS capsular saccharide may be present at an amount from 0.5 to 5 μg, 1 to 4 μg, 2 to 3 μg, or about 2.5 μg per unit dose.

In the embodiments described above wherein the immunogenic composition comprises more than one conjugate, the ratio of the mass of a given capsular saccharide to the mass of the other capsular saccharide(s) may vary. However, typically the ratio of the masses of the GBS serotype Ia, Ib, II, III and V capsular saccharides is 1:1:1:1:1.

Methods of administering the immunogenic compositions of the invention are discussed below. Briefly, the immunogenic compositions of the invention may be administered in single or multiple doses. The administration of a single dose of the immunogenic compositions of the invention is effective. Administration of a single dose is therefore preferred in the invention, particularly for these embodiments.

Alternatively, one unit dose followed by a second unit dose may be effective. Typically, the second (or third, fourth, fifth etc.) unit dose is identical to the first unit dose. The second unit dose may be administered at any suitable time after the first unit dose, in particular after 1, 2 or 3 months. For example, the second unit dose may be administered 3 months after the first unit dose. In another example, the second unit dose may be administered 1 month after the first unit dose. Typically, the immunogenic compositions of the invention will be administered intramuscularly, e.g. by intramuscular administration to the thigh or the upper arm as described below.

As described below, immunogenic compositions of the invention may include one or more adjuvants. However, the use of unadjuvanted compositions can also be effective. It may be advantageous to omit adjuvants in order to reduce potential toxicity. Accordingly, immunogenic compositions that do not contain any adjuvant (especially that do not contain any aluminium salt adjuvant) are preferred for use in the invention, particularly for these embodiments.

The Capsular Saccharide

The invention is based on the capsular saccharide of *Streptococcus agalactiae*. The capsular saccharide is covalently linked to the peptidoglycan backbone of GBS, and is distinct from the group B antigen, which is another saccharide that is attached to the peptidoglycan backbone.

The GBS capsular saccharides are chemically related, but are very different from an antigenic standpoint. All GBS capsular polysaccharides share the following trisaccharide core:

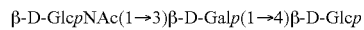

β-D-Glc*p*NAc(1→3)β-D-Gal*p*(1→4)β-D-Glc*p*

The various GBS serotypes differ by the way in which this core is modified. The difference between serotypes Ia and III, for instance, arises from the use of either the GlcNAc (Ia) or the Gal (III) in this core for linking consecutive trisaccharide cores. Serotypes Ia and Ib both have a [α-D-NeupNAc(2→3)β-D-Gal*p*-(1→] disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 85% being caused by five serotypes: Ia, Ib, III & V. The invention preferably uses a saccharide from one or more of these four serotypes, particularly from one or more of serotypes: Ia, Ib & III. The capsular saccharides of each of these four serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

All four saccharides include galactose residues within the trisaccharide core, but serotypes Ia, Ib, II & III also contain additional galactose residues in each repeating unit.

The saccharide may be chemically modified relative to the capsular saccharide as found in nature. For example, the saccharide may be de-O-acetylated (partially or fully), de-N-acetylated (partially or fully), N-propionated (partially or fully), etc. De-acetylation may occur before, during or after conjugation, but preferably occurs before conjugation. Depending on the particular saccharide, de-acetylation may or may not affect immunogenicity. The relevance of O-acetylation on GBS saccharides in various serotypes is discussed in reference 12, and in some embodiments O-acetylation of sialic acid residues at positions 7, 8 and/or 9 is retained before, during and after conjugation e.g. by protection/de-protection, by re-acetylation, etc. However, typically the GBS saccharide used in the present invention has substantially no O-acetylation of sialic acid residues at positions 7, 8 and/or 9. In particular, when the GBS saccharide has been purified by base extraction as described below, then O-acetylation is typically lost (ref. 12). The effect of de-acetylation etc. can be assessed by routine assays. The serotype V capsular saccharide may be modified as described in refs. 13 and 14. For example, a serotype V capsular saccharide that has been substantially desialylated as described in refs. 13 and 14 can be useful. Desialylated GBS serotype V capsular saccharide may be prepared by treating purified GBS serotype V capsular saccharide under mildly acidic conditions (e.g. 0.1M sulphuric acid at 80° C. for 60 minutes) or by treatment with neuraminidase, as described in reference 13. A preferred method for preparing desialylated GBS serotype V capsular saccharide is by treating the purified saccharide with IM acetic acid at 81° C.+/−3 C° for 2 h.

Particularly the degree of sialic acid oxidation of the GBS serotype V capsular polysaccharide is less than 40%, less than 25%, less than 20%, less than 17%, less than 15%, less than 10%, for example, about 12%, about 9%, about 8%, about 7%. Particularly the N-acetyl-neuraminic acid (NeuNAc or sialic acid) content of the GBS serotype V capsular polysaccharide is greater than 50%, greater than 60%, greater than 70%, greater than 75%, greater than 80%, greater than 85%, greater than 90%, greater than 95%, when compared to native GBS serotype V polysaccharide wherein the NeuNAc content is considered to be about 100%. Particularly, the GBS serotype V polysaccharide is a fully sialylated or "native polysaccharide". For example, with a sialic acid content of about 100%, 99%, 98%, 97%, 96%, 95%, 94%, 93%, 92%, 91%, about 90% (or any range between these values) when compared to native GBS serotype V polysaccharide. Particularly, the type v polysaccharide contains D-glucose, D-galactose, 2-acetamido-2-deoxyglucose and sialic acid in a molar ratio of 3:2:1:1.

The saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. Chain length has been reported to affect immunogenicity of GBS saccharides in rabbits [4]. In particular, the serotype II and/or III capsular saccharides used in the invention may be depolymerised as described in refs. 15 and 16. These documents describe the partial depolymerization of type II and type III capsular saccharides by mild deaminative cleavage to antigenic fragments with reducing-terminal 2,5-anhydro-D-mannose residues. Briefly, the capsular saccharide is dissolved in 0.5N NaOH and heated at 70° C. for between about 1-4 h. The length of this incubation controls the degree of depolymerisation, which may be determined by standard methods (e.g. by HPLC as described in reference 15). The sample is chilled in an ice-water bath before glacial acetic acid is added to bring the pH to 4. The partially N-deacylated product is then deaminated by the addition of 5% (wt/vol) $NaNO_2$ with stirring at 4° C. for 2 h. The free aldehydes of the newly formed 2,5-anhydro-D-mannose residues may be used for conjugation to a carrier protein, as described below.

Depolymerisation of the serotype III capsular saccharide by endo-β-galactosidase has been reported [refs. 1 & 4-6], including using the depolymerised material to form conjugates with a tetanus toxoid carrier. Ozonolysis of capsular polysaccharides from GBS serotypes III and VIII has also been used for depolymerisation [17]. It is preferred to use saccharides with MW>30 kDa, and substantially full-length capsular polysaccharides can be used. For serotype Ia, it is preferred to use polysaccharides with a MW in the range of 150-300 kDa, particularly 175-275 kDa. Typically, a serotype Ia saccharide with MW about 200 kDa or about 260 kDa is used. For serotype Ib, it is preferred to use polysaccharides with a MW in the range of 150-300 kDa, particularly 175-250 kDa. Typically, a serotype Ib saccharide with MW about 200 kDa or about 230 kDa is used. For serotype III, it is preferred to use polysaccharides with a MW in the range of 50-200 kDa, particularly 80-150 kDa. Typically, a serotype III saccharide with MW about 100 kDa or about 140 kDa is used. For serotype V, it is also preferred to use polysaccharides with a MW up to ~50 kDa. Typically, a serotype V saccharide with MW about 100 kDa is used. These molecular masses can be measured by gel filtration relative to dextran standards, such as those available from Polymer Standard Service [18].

Capsular saccharides can be purified by known techniques, as described in the references herein such as refs. 2 and 19. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in reference 20 can be used. This involves base extraction, ethanol/$CaCl_2$ treatment, CTAB precipitation, and re-solubilisation. A further alternative process is described in reference 21.

The invention is not limited to saccharides purified from natural sources, however, and the saccharides may be obtained by other methods, such as total or partial synthesis.

Conjugation

The invention involves conjugates that are capsular saccharides from GBS serotypes Ia, Ib, II, III and V, each conjugated to a carrier protein. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 22] and is a well known technique [e.g. reviewed in refs. 23 to 31]. Thus the processes of the invention may include the further step of conjugating the purified saccharide to a carrier molecule.

Conjugation of GBS saccharides has been widely reported e.g. see reference 1. Although polysaccharides are immunogenic, conjugation of polysaccharides to carrier proteins can improve or enhance immunogenicity. Therefore, as used herein, the term "carrier" refers to an immunogenic substance which, when conjugated to an antigen (such as a polysaccharide) and administered to an animal, will induce or enhance an immune response in the animal, particularly a protective immune response, and elicit the production of antibodies that bind specifically to the antigen, for example, the above described polysaccharides. The typical prior art process for GBS saccharide conjugation typically involves reductive amination of a purified saccharide to a carrier protein such as tetanus toxoid (TT) or CRM197 [2]. The reductive amination involves an amine group on the side chain of an amino acid in the carrier and an aldehyde group in the saccharide. As GBS capsular saccharides do not include an aldehyde group in their natural form then this is typically generated before conjugation by oxidation (e.g. periodate oxidation) of a portion (e.g. between 5 and 40%, particularly between 10 and 30%, preferably about 20%) of the saccharide's sialic acid residues [2,32]. Conjugate vaccines prepared in this manner have been shown to be safe and immunogenic in humans for each of GBS serotypes Ia, Ib, II, III, and V [10]. Typically, all of the conjugates in the immunogenic compositions of the present invention have been prepared in this manner. However, when the invention uses a serotype V capsular saccharide that is desialylated, then an aldehyde group may be generated in this saccharide before conjugation by oxidation (e.g. periodate oxidation) of a portion (e.g. between 5 and 40%, particularly between 10 and 30%, preferably about 20%) of the saccharide's galactose residues [14]. An alternative conjugation process involves the use of $—NH_2$ groups in the saccharide (either from de-N-acetylation, or after introduction of amines) in conjunction with bifunctional linkers, as described in ref. 33. In some embodiments, one or more of the conjugates in the immunogenic compositions of the present invention have been prepared in this manner. A further alternative process is described in refs. 15 and 16. In this process, the free aldehydes groups of terminal 2,5-anhydro-D-mannose residues from depolymerization of type II or type III capsular saccharides by mild deaminative cleavage are used for conjugation by reductive amination. In some embodiments, one or more of the conjugates in the immunogenic compositions of the present invention have been prepared in this manner.

The invention involves the use of carrier molecules, which are typically proteins. Useful carrier proteins include bacterial toxins or toxoids, such as *diphtheria* toxoid or tetanus toxoid. Fragments of toxins or toxoids can also be used e.g. fragment C of tetanus toxoid [34].

The CRM197 mutant of *diphtheria* toxin [35-37] is a particularly useful carrier for use with the invention. The cross-reacting material (CRM197) is a genetically detoxified preparation of *diphtheria* toxin. CRM197 differs from *diphtheria* toxin (DT) in only a single amino acid and is therefore highly cross-reactive with DT (CRM=cross reactive material). This mutant of *diphtheria* toxin does not require detoxification with formaldehyde, and homogeneous preparations of purified antigen can be readily obtained, for example, from cultures of *Corynebacterium diphtheria* strain C7 (beta197) grown in casamino acids and yeast extract medium. Alternatively CRM197 may be prepared recombinantly in accordance with U.S. Pat. No. 5,614,382. CRM197 is licensed for human use as a carrier protein for several capsular polysaccharide antigens and is a potential alternative to conventional *diphtheria* toxoid prepared by formaldehyde treatment.

Other suitable carrier proteins include the *N. meningitidis* outer membrane protein [38], synthetic peptides [39,40], heat shock proteins [41,42], pertussis proteins [43,44], cytokines [45], lymphokines [45], hormones [45], growth factors [45], human serum albumin (preferably recombinant), artificial proteins comprising multiple human CD4+ T cell epitopes from various pathogen-derived antigens 1461 such as N19 [47], protein D from *H. influenzae* [48,49], pneumococcal surface protein PspA [50], pneumolysin [51], iron-uptake proteins [52], toxin A or B from *C. difficile* [53], recombinant *Pseudomonas aeruginosa* exoprotein A (rEPA) [54], etc.

Attachment to the carrier is preferably via a $—NH_2$ group e.g. in the side chain of a lysine residue in a carrier protein, or of an arginine residue, or at the N-terminus. Attachment may also be via a $—SH$ group e.g. in the side chain of a cysteine residue.

It is possible to use more than one carrier protein e.g. to reduce the risk of carrier suppression. Thus different carrier proteins can be used for different GBS serotypes e.g. serotype Ia saccharides might be conjugated to CRM197 while serotype Ib saccharides might be conjugated to tetanus toxoid.

Particularly, serotype Ia, Ib and III saccharides might be conjugated to a first carrier, such as CRM197, while serotype II and V saccharides might be conjugated to a second (different) carrier, such as tetanus toxoid (-TT). Yet more particularly, serotype Ia, Ib, III and V saccharides might be conjugated to a first carrier, such as CRM197, while serotype II saccharides might be conjugated to a second (different) carrier, such as -TT.

An exemplary immunogenic composition of the invention comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; d) a conjugate that is a capsular saccharide from GBS serotype II conjugated to CRM197; and c) a conjugate that is a capsular saccharide from GBS serotype V conjugated to CRM197. Another exemplary immunogenic composition of the invention comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; d) a conjugate that is a capsular saccharide from GBS serotype II conjugated to tetanus toxoid; and e) a conjugate that is a capsular saccharide from GBS serotype V conjugated to tetanus toxoid. Yet another exemplary immunogenic composition of the invention comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; d) a conjugate that is a capsular saccharide from GBS serotype II conjugated to tetanus toxoid; and e) a conjugate that is a capsular saccharide from GBS serotype V conjugated to CRM197. Still yet another exemplary immunogenic composition of the invention comprises (a) a conjugate that is a capsular saccharide from GBS serotype Ia conjugated to CRM197; b) a conjugate that is a capsular saccharide from GBS serotype Ib conjugated to CRM197: c) a conjugate that is a capsular saccharide from GBS serotype III conjugated to CRM197; d) a conjugate that is a capsular saccharide from GBS serotype II conjugated to CRM197; and e) a conjugate that is a capsular saccharide from GBS serotype V conjugated to tetanus toxoid. It is also possible to use more than one carrier protein for a particular saccharide antigen e.g. serotype III saccharides might be in two groups, with some conjugated to CRM197 and others conjugated to tetanus toxoid. In general, however, it is preferred to use the same carrier protein for all saccharides.

A single carrier protein might carry more than one saccharide antigen [55,56]. For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

Conjugates with a saccharide:protein ratio (w/w) of between 1:5 (i.e. excess protein) and 5:1 (i.e. excess saccharide) are typically used, in particular ratios between 1:5 and 2:1. For the conjugate that is a capsular saccharide from GBS serotype Ia conjugated to a carrier protein, the saccharide:protein ratio (w/w) is typically between about 1:1 to 1:2, particularly about 1:1.3. For the conjugate that is a capsular saccharide from GBS serotype Ib conjugated to a carrier protein, the ratio is typically between about 1:1 to 1:2, particularly about 1:1.3. For the capsular saccharide from GBS serotype III conjugated to a carrier protein, the saccharide:protein ratio (w/w) is typically between about 3:1 to 1:1, particularly about 2:1. However, GBS serotype III conjugated to a carrier protein with a saccharide:protein ratio (w/w) of about 1:1 to 1:5, particularly about 1:3.3, may also be used. For the conjugate that is a capsular saccharide from GBS serotype V conjugated to a carrier protein, then the ratio is typically between about 2:1 to 1:1, particularly about 1.1:1. Thus a weight excess of saccharide is typical, particularly with longer saccharide chains.

If desialylated GBS serotype V polysaccharide is used, particularly different levels of polysaccharide to protein cross-linking are used. The level of cross-linking may be modulated, for example, by varying the protein-polysaccharide ratio. Particularly, the saccharide:protein ratio (w/w) is less than 1:1.5, less than 1:1, less than or about 1:0.5.

Compositions may include a small amount of free carrier [57]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated saccharides can be separated. There are many suitable methods, including hydrophobic chromatography, tangential ultrafiltration, diafiltration etc. [see also refs. 58 & 59, etc.]. A preferred method is described in reference 60.

Where the composition of the invention includes a depolymerised oligosaccharide, it is preferred that depolymerisation precedes conjugation.

Pharmaceutical Methods and Uses

The immunogenic compositions of the invention may further comprise a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [61], trehalose [62], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present Sterile pyrogen-free, phosphate-buffered physiologic saline is a typical carrier. A thorough discussion of pharmaceutically acceptable excipients is available in reference 63.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form. When the immunogenic compositions of the invention include conjugates comprising capsular saccharides from more than one GBS semtypes, it is typical for the conjugates to be prepared separately, mixed and then lyophilised. In this way, lyophilised compositions comprising two, three or four etc. conjugates as described herein may be prepared. To stabilise conjugates during lyophilisation, it may be preferred to include a sugar alcohol (e.g. mannitol) and/or a disaccharide (e.g. sucrose or trehalose) e.g. at between 1 mg/ml and 30 mg/ml (e.g. about 25 mg/ml) in the composition. The use of sucrose has been recommended as a stabiliser for GBS conjugate vaccines (ref. 64). However, it is typical for the stabiliser of the present invention to be mannitol. When the dried vaccine is reconstituted into a liquid medium prior to injection, the concentration of residual mannitol will typically be about 2-20 mg/ml, e.g. 3.75 mg/ml, 7.5 mg/ml or 15 mg/ml. The use of mannitol is advantageous because mannitol is chemically distinct from the monosaccharide subunits of the GBS capsular saccharides. This means that detection of the capsular saccharides, e.g. for quality control analysis, can be based on the presence of the subunits of the saccharides without interference from the mannitol. In contrast, a stabiliser like sucrose contains glucose, which may interfere with the detection of glucose subunits in the saccharides.

Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. The immunogenic compositions of the invention typically comprise a potassium dihydrogen phosphate buffer. The potassium dihydrogen phosphate buffer may comprise about 1-10 mM potassium dihydrogen phosphate, e.g. 1.25 mM, 2.5 mM or 5.0 mM. If a composition comprises an aluminium hydroxide salt, it is preferred to use a histidine buffer [65]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Compositions of the invention are immunogenic, and are more preferably vaccine compositions. Vaccines according to the invention may either be prophylactic (i.e. to prevent infection) or therapeutic (i.e. to treat infection), but will typically be prophylactic. Prophylactic vaccines do not guarantee complete protection from disease because even if the patient develops antibodies, there may be a lag or delay before the immune system is able to fight off the infection. Therefore, and for the avoidance of doubt, the term prophylactic vaccine may also refer to vaccines that ameliorate the effects of a future infection, for example by reducing the severity or duration of such an infection. The terms "protection against infection" and/or "provide protective immunity" means that the immune system of a subject has been primed (e.g by vaccination) to trigger an immune response and repel infection. Particularly, the immune response triggered is capable of repelling infection against a number of pathogens, such as different strains of bacteria. A vaccinated subject may thus get infected, but is better able to repel the infection than a control subject.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. Commonly, the desired result is the production of an antigen (e.g., pathogen)-specific immune response that is capable of or contributes to protecting the subject against the pathogen. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 0.1-50 µg (measured as mass of saccharide), particularly between 1-50 µg or 0.5-25 µg, more particularly 2.5-7.5 µg, e.g. about 1 µg, about 2.5 µg, about 5 µg, about 10 µg, about 15 µg, about 20 µg or about 25 µg. Within each dose, the total quantity of CBS capsular saccharides will generally be ≤70 µg (measured as mass of saccharide), e.g. ≤60 µg. In particular, the total quantity may be ≤40 µg (e.g. ≤30 µg) or ≤20 µg (e.g. ≤15 µg). These total quantities are preferred for use in the invention. It may be advantageous to minimise the total quantity of capsular saccharide(s) per unit dose in order to reduce potential toxicity. Accordingly, a total quantity of ≤20 µg is preferred, e.g. ≤15 µg, ≤7.5 µg or ≤1.5 µg.

GBS affects various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 66 & 67]. Success with nasal administration of pneumococcal saccharides [68,69], Hib saccharides [70], MenC saccharides [71], and mixtures of Hib and MenC saccharide conjugates [72] has been reported.

Compositions of the invention may be combined with aP/wP, TT, DT and/or IPV antigens, i.e. acellular pertussis antigens, for example pertussis filamentous hemagglutinin (FHA), pertactin (PRN, 69K-OMP), pertussis fimbriac (FIM), or cellular pertussis antigens, whole cell pertussis antigens, pertussis toxoid or pertussis toxin (PT), tetanus toxoid, *diphtheria* toxoid and/or Inactivated poliovirus antigen. For example, this could be carried out by combining compositions of the invention with already commercially available formulations including ANATETALL® (Toxoid Vaccine Adsorbed), DIF-TET-ALL® (*Diphtheria* and Tetanus Toxoids Adsorbed), PENTACEL® (*Diphtheria* and Tetanus Toxoids and Acellular Pertussis Adsorbed, Inactivated Poliovirus and *Haemophilus* b Conjugate) or DAPTACEL® (*Diphtheria* and Tetanus Toxoids and Acellular Pertussis Vaccine Adsorbed).

Compositions of the invention may include an antimicrobial, particularly when packaged in multiple dose formats.

Compositions of the invention may comprise detergent e.g. a TWEEN® (polysorbate), such as TWEEN® 80 (polyoxyethylenesorbitan monooleate). Detergents are generally present at low levels e.g. <0.01%.

Compositions of the invention may include sodium salts (e.g. sodium chloride) to give tonicity. A concentration of 10±2 mg/ml NaCl is typical. In some embodiments, a concentration of 4-10 mg/ml NaCl may be used, e.g. 9.0, 7.0, 6.75 or 4.5 mg/ml.

Compositions of the invention will generally include a buffer. A phosphate buffer is typical.

Compositions of the invention may be administered in conjunction with other immunoregulatory agents.

In particular, compositions may include one or more adjuvants. Such adjuvants include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in ref. 73). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [74].

The adjuvants known as aluminum hydroxide and aluminum phosphate may be used. These names are conventional, but are used for convenience only, as neither is a precise description of the actual chemical compound which is present (e.g. see chapter 9 of reference 75). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pi of aluminium hydroxide adjuvants is typically about 11 i.e. the adjuvant itself has a positive surface charge at physiological pH. Adsorptive capacities of between 1.8-2.6 mg Aluminium phosphate adjuvants generally have a $PO_4/Al$ molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $A^{3+}$/ml. The aluminium phosphate will generally be particulate (e.g. plate-like morphology as seen in transmission electron micrographs). Typical diameters of the particles are in the range 0.5-20-tm (e.g. about 5-10-tm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. 15 about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≥5 mg/ml, ≥4 mg/ml, ≥2 mg/ml, ≥1 mg/ml, etc. A preferred range is between 0.3 and 1 mg/ml. A maximum of 0.85 mg/dose is preferred.

A typical adjuvant aluminium phosphate adjuvant is amorphous aluminium hydroxyphosphate with $PO_4/Al$ molar ratio between 0.84 and 0.92, included at 0.6 mg $A^{3+}$/ml. Adsorption with a low dose of aluminium phosphate may be used e.g. between 50 and 100 µg $Al^{3+}$ per conjugate per dose.

B. Oil Emulsions

Oil emulsion compositions suitable for use as adjuvants in the invention include squalene-water emulsions, such as MF59® (5% squalene, 0.5% TWEEN® 80 (polyoxyethylenesorbitan monooleate), and 0.5% SPAN® (sorbitan trioleate) 85, formulated into submicron particles using a microfluidizer) [Chapter 10 of ref. 75; see also refs. 76-78]. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN® 80 (polyoxyethylenesorbitan monooleate), and/or 0.25-1.0% SPAN® 85 (sorbitan trioleate), and, optionally, N-acetylmuramyl-L-alanyl-D-isogluatminyl-L-alanine-2-(1'-2'-dipalmitoyl-sn-glycero-3-hydroxyphosphophoryloxy)-ethylamine (MTP-PE). Submicron oil-in-water emulsions, methods of making the same and immunostimulating agents, such as muramyl peptides, for use in the compositions, are described in detail in references 76 & 79-80.

Complete Freund's adjuvant (CFA) and incomplete Freund's adjuvant (IFA) may also be used as adjuvants in the invention.

C. Saponin Formulations [Chapter 22 of Ref 75]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 81. Saponin formulations may also comprise a sterol, such as cholesterol [82].

Combinations of saponins and cholesterols can be used to form unique particles called immunostimulating complexs (ISCOMs) [chapter 23 of ref. 75]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 82-84. Optionally, the ISCOMS may be devoid of additional detergent(s) [85].

A review of the development of saponin based adjuvants can be found in refs. 86 & 87.

D. Virosomes and Virus-Like Particles

Virosomes and virus-like particles (VLPs) can also be used as adjuvants in the invention. These structures generally contain one or more proteins from a virus optionally combined or formulated with a the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages. Qβ-phage (such as coat proteins), GA-phage, fr-phage, AP205 phage, and Ty (such as retrotransposon Ty protein p1). VLPs are discussed further in refs. 88-93. Virosomes are discussed further in, for example, ref 94

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 95. Such "small particles" of 3dMPL are small enough to be sterile filtered through a 0.22 µm membrane [95]. Other non-toxic LPS derivatives include monophosphoryl lipid A mimics, such as aminoalkyl glucosaminide phosphate derivatives e.g. RC-529 [96.97].

Lipid A derivatives include derivatives of lipid A from *Escherichia coli* such as OM-174. OM-174 is described for example in refs. 98 & 99.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 100, 101 and 102 disclose possible analog substitutions e.g. replacement of guanosine with 2'-deoxy-7-deazaguanosine. The adjuvant effect of CpG oligonucleotides is further discussed in refs. 103-108.

The CpG sequence may be directed to TLR9, such as the motif GTCGTT or TTCGTT [109]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 110-112. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers." See, for example, refs. 109 & 113-115.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 116 and as parenteral adjuvants in ref. 117. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 118-125. Numerical reference for amino acid substitutions is preferably based on the alignments of the A and B subunits of ADP-ribosylating toxins set forth in ref. 126, specifically incorporated herein by reference in its entirety.

F. Human Immunomodulators

Human immunomodulators suitable for use as adjuvants in the invention include cytokines, such as interleukins (e.g. IL-1. IL-2, IL-4, IL-5, IL-6, IL-7. IL-12 [127], etc.) [128], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [129] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [130].

H. Microparticles

Microparticles may also be used as adjuvants in the invention. Microparticles (i.e. a particle of ~100 nm to ~150 µm in diameter, more preferably ~200 nm to ~301 µm in diameter, and most preferably ~500 nm to ~101 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 75)

Examples of liposome formulations suitable for use as adjuvants are described in refs. 131-133.

J. Polyoxyethylene Ether and Polyoxyethylene Ester Formulations

Adjuvants suitable for use in the invention include polyoxyethylene ethers and polyoxyethylene esters [134]. Such formulations further include polyoxyethylene sorbitan ester surfactants in combination with an octoxynol [135] as well as polyoxyethylene alkyl ethers or ester surfactants in combination with at least one additional non-ionic surfactant such as an octoxynol [136]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 137 and 138.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 139 and 140.

N. Thiosemicarbazone Compounds.

Examples of thiosemicarbazone compounds, as well as methods of formulating, manufacturing, and screening for compounds all suitable for use as adjuvants in the invention include those described in ref. 141. The thiosemicarbazones are particularly effective in the stimulation of human peripheral blood mononuclear cells for the production of cytokines, such as TNF-α.

O. Tryptanthrin Compounds.

Examples of tryptanthrin compounds, as well as methods of formulating, manufacturing, and screening for compounds all suitable for use as adjuvants in the invention include those described in ref. 142. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following combinations may be used as adjuvant compositions in the invention: (1) a saponin and an oil-in-water emulsion [143]; (2) a saponin (e.g. QS21)+a non-toxic LPS derivative (e.g. 3dMPL) [144]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [145]; (5) combinations of 3dMPL with, for example, QS21 and/or oil-in-water emulsions [146]; (6) SAF, containing 10% squalane, 0.4% Tween 80™. 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 75.

The use of aluminium salt adjuvants is particularly preferred, and antigens are generally adsorbed to such salts. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc. A preferred class of humans for treatment are females of child-bearing age (e.g. teenagers and above). Another preferred class is pregnant females. Elderly patients (e.g. those above 50, 60, 70, 80 or 90 etc. years of age, particularly over 65 years of age), especially those living in nursing homes where the risk of GBS infection may be increased ([147]), are another preferred class of humans for treatment. In some embodiments, the human has an undetectable level of antibodies against capsular saccharide from GBS serotype Ia prior to administration of the pharmaceutical composition. In other embodiments, the human has an undetectable level of antibodies against capsular saccharide from GBS serotype Ib prior to administration of the pharmaceutical composition. In other embodiments, the human has an undetectable level of antibodies against capsular saccharide from GBS serotype III prior to administration of the pharmaceutical composition. In other embodiments, the human has an undetectable level of antibodies against capsular saccharide from GBS serotype II prior to administration of the pharmaceutical composition. In other embodiments, the human has an undetectable level of antibodies against capsular saccharide from GBS serotype V prior to administration of the pharmaceutical composition. In particular, the human may have an undetectable level of antibodies against capsular saccharide from GBS serotype Ia and an undetectable level of antibodies against capsular saccharide from GBS serotype Ib prior to administration of the pharmaceutical composition. Alternatively or in addition, the human may have an undetectable level of antibodies against capsular saccharide from GBS serotype III prior to administration of the pharmaceutical composition. Alternatively or in addition, the human may have an undetectable level of antibodies against capsular saccharide from GBS serotype II prior to administration of the pharmaceutical composition. Alternatively or in addition, the human may have an undetectable level of antibodies against capsular saccharide from GBS serotype V prior to administration of the pharmaceutical composition. The level(s) of antibodies against the capsular saccharide(s) may be determined using techniques that are known in the art, e.g. ELISA. The level(s) of antibodies may be as of one month prior to administration, particularly within one month prior to administration (e.g. within two weeks, within one week or on the day of administration). Women with these undetectable level(s) of antibodies against the capsular saccharide(s) may have higher rates of GBS infection in their newborns. This is because higher levels of maternal antibodies against GBS capsular saccharides are correleated with reduced risk of disease in newborns [refs. 148 and 149]. Accordingly, administration to these women is specifically envisaged in the present invention.

The invention also provides a composition of the invention for use as a medicament. The medicament is preferably able to raise an immune response in a mammal (i.e. it is an immunogenic composition) and is more preferably a vaccine.

The invention also provides the use of a composition of the invention in the manufacture of a medicament for raising an immune response in a mammal.

These uses and methods are preferably for the prevention and/or treatment of a disease caused by *S. agalactiae* e.g. neonatal sepsis or bacteremia, neonatal pneumonia, neonatal meningitis, endometritis, osteomyelitis, septic arthritis, etc.

The subject in which disease is prevented may not be the same as the subject that receives the conjugate of the invention. For instance, a conjugate may be administered to a female (before or during pregnancy) in order to protect offspring (so-called 'maternal immunisation' [150-152]). The immunization of the pregnant female provides antibody-mediated immunity to the infant through passive maternal immunity. The passive immunity occurs naturally when maternal antibodies are transferred to the fetus through the placenta. Passive immunity is especially important to infants because they are born without any actively acquired immunity. Administration of compositions of the invention to a pregnant female enhances immunity in the female, and antibodies are passed to the newborn through the placenta, conferring passive maternal immunity on the infant. However, passive immunity in infants is only temporary and starts to decrease after the first few weeks, or months of life. As passive immunity is only temporary, it may be important for the infant to receive administration of a composition of the invention, to induce active immunity in the infant, before the passive immunity diminishes. Administration of a second immunogenic composition to the infant after birth induces active immunity in the infant, and extends the immunity passed on from the mother during pregnancy.

As used herein, an infant is an individual under one year of age (e.g., less than one day old, 1 week old, 2 weeks old, 3 weeks old, 4 weeks old, 2 months old, 3 months, 4 months, 5 months, 6 months, 7 months, 8 months old, 9 months old, 10 months old, 11 months old, less than 12 months old).

The pregnant female may be administered the composition of the invention at any time during her pregnancy. For example, the composition may be administered to the female during the first, second or third trimester of her pregnancy. In some embodiments, the composition is administered to the female during the last 6-12 weeks of the pregnancy (e.g., 28 weeks gestation, 29 weeks gestation, 30 weeks gestation, 31 weeks gestation, 32 weeks gestation, 33 weeks gestation, 34 weeks gestation, 35 weeks gestation, 36 weeks gestation, 37 weeks gestation, 38 weeks gestation, 39 weeks gestation). Particularly, the composition of the invention is administered to the pregnant female at least four weeks before delivery of the infant. In some embodiments, a one-dose regimen is administered to the pregnant female between weeks 32 and 36 gestation. In other embodiments, a two-dose regimen is administered to the pregnant female, with the first dose being administered at approximately 32 weeks gestation and the second dose being administered at approximately 36 weeks gestation.

The infant may be administered the composition at any time during the first year of life, and thereafter if desired. Generally the composition will be administered to the infant one, two, three, four or more times during the first year of life. For example, the composition of the invention may be administered to the infant one or more times selected from at birth, at 2 weeks old, 4 weeks old, 6 weeks old, 2 months old, 3 months old, 4 months old, 6 months old, 9 months old, and 12 months old. Particularly, the composition of the invention is administered to the infant at a time before maternal antibodies have decreased to non-protective titers. Subsequent administrations can occur on any desired schedule.

In one embodiment, there is provided a method of protecting an infant against a disease caused by *Streptococcus agalactiae* comprising the steps of (a) administering a composition of the invention to a female during pregnancy with said infant; and (b) optionally administering a composition of the invention to the infant that is born from the pregnancy. Particularly, a method of protecting an infant against Early Onset disease caused by *Streptococcus agalactiae* serotypes Ia, Ib, III, II and V. Particularly the disease is sepsis occurring within 0 and 168 hours of birth, yet more particularly 0 and 72 hours of birth, still yet more particularly between 24 and 72 hours of birth, and still yet more particularly between 48 and 72 hours of birth.

There is also provided a method of protecting an infant against Late Onset disease caused by *Streptococcus agalactiae* serotypes Ia, Ib, III, II and V. Particularly the disease occurs within 7 days to 90 days of birth or later.

One way of checking efficacy of therapeutic treatment involves monitoring GBS infection after administration of the composition of the invention. One way of checking efficacy of propylactic treatment involves monitoring immune responses against the GBS antigens after administration of the composition.

Preferred compositions of the invention can confer an antibody titre in a patient that is superior to the criterion for seroprotection for each antigenic component for an acceptable percentage of human subjects. Antigens with an associated antibody liter above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 mL Administration to the pregnant female and the infant may be through the same route or different routes.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The term "comprising" encompasses "including" as well as "consisting" e.g. a composition "comprising" X may consist exclusively of X or may include something additional e.g. X+Y.

The term "consisting of" means "consisting only of". A composition "consisting of X" may not include any other components. A composition "consisting essentially of X" may not include any other active components. The term "consisting essentially of" means that the composition, method or structure may include additional ingredients, steps and/or parts, but only if the additional ingredients, steps and/or parts do no materially alter the basic and novel characteristics of the claimed composition, method or structure.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

Unless specifically stated, a process comprising a step of mixing two or more components does not require any specific order of mixing. Thus components can be mixed in any order. Where there are three components then two components can be combined with each other, and then the combination may be combined with the third component, etc.

Antibodies will generally be specific for their target. Thus they will have a higher affinity for the target than for an irrelevant control protein, such as bovine serum albumin.

Unless otherwise stated, identity between polypeptide sequences is preferably determined by the Smith-Waterman homology search algorithm as implemented in the MPSRCH program (Oxford Molecular), using an affine gap search with parameters gap open penalty=12 and gap extension penalty=1.

MODES FOR CARRYING OUT THE INVENTION

Vaccines

GBS monovalent vaccines used in Studies 1-4 are all conjugated to CRM197.

The GBS trivalent vaccine used in all studies is composed of capsular polysaccharides derived from serotypes: Ia, Ib and III, each conjugated to CRM197.

Study 1

Figure 1:
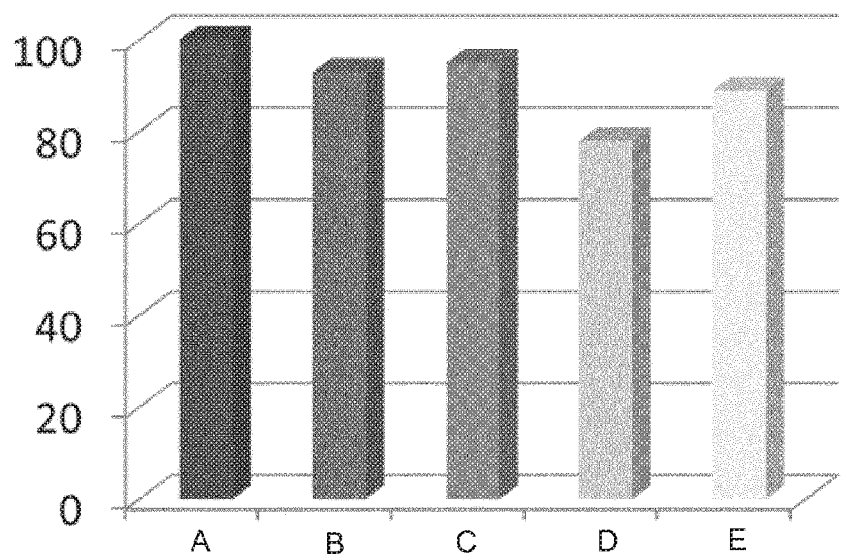
FIG. 1 shows the survival of mice (% protection) in a neonatal challenge model. Maternal immunisation was carried out with (A) GBS Ia, (B) GBS Ib, (C) GBS III, (D) GBS II and (E) GBS V, each conjugated to CRM197. Mice were challenged with the corresponding antigen.

The level of protection of mice in a neonatal challenge model (Maione et al., Science 1 Jul. 2005: vol. 309 no. 5731 pp. 148-150) was investigated. Three doses of GBS monovalent vaccines (1 μg antigen) adjuvanted with aluminium salt (400 μg) were given to the mothers. The GBS monovalent vaccines tested were GBS Ia, Ib, 11, 111 and V, each conjugated to CRM197. The results are shown in FIG. 1.

Figure 2:
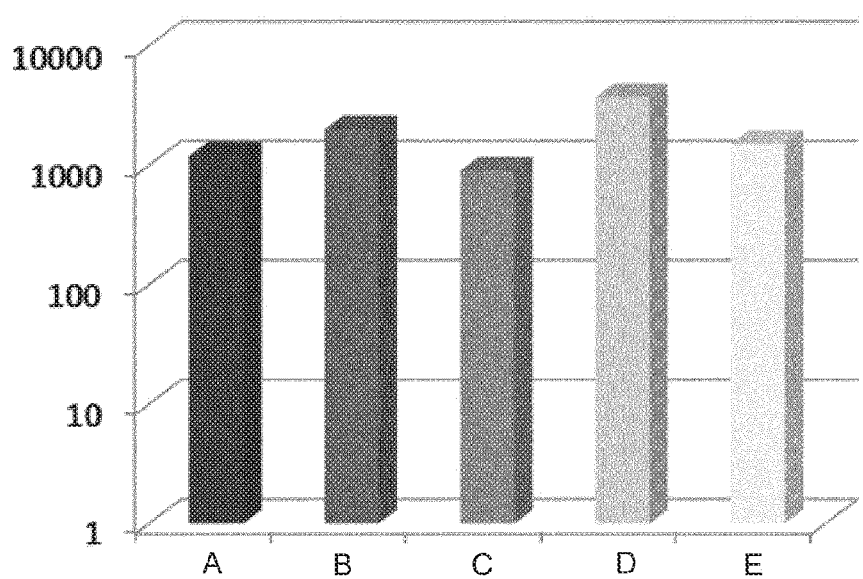
FIG. 2 shows the OPK titers against (A) GBS Ia, (B) GBS Ib, (C) GBS III, (D) GBS II and (E) GBS, each conjugated to CRM197. Mice were immunised with the corresponding antigen.

OPK assays were also carried out, and the results are shown in FIG. 2. A viable approach to assess a vaccine's efficacy is to use a surrogate of protection which in the case of GBS is the opsonizing activity of serum antibody. The opsonophagocytosis killing assay measures the ability of serum antibody to opsonize GBS for killing by effector cells in the presence of complement. Generally, there is good correlation between ELISA IgG Abs and OPK titers. It can be seen that protection and OPA levels by GBS II and GBS V are comparable to those by GBS Ia, Ib and III.

Study 2

Mice were immunised with three doses of mono- or multivalent vaccines (1 μg of each antigen) adjvuanted with aluminium salt (400 Mg). The vaccines tested were (1) CBS V, (2) a tetravalent vaccine containing GBS V and the GBS trivalent vaccine, and (3) a pentavalent vaccine containing GBS II, GBV and the GBS trivalent. Mice were immunised with aluminium salt alone as a negative control. ELISA and OPK assays (using type V CJB111 strain) were carried out (repeated twice).

Figure 3A:
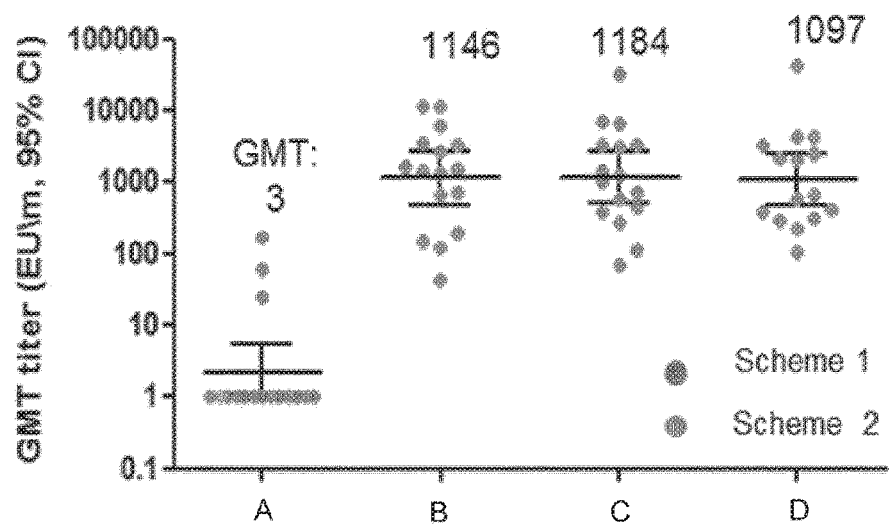
FIG. 3 shows IgG titers (FIG. 3A) and OPK titers (FIG. 3B) against GBS V. Mice were immunised with (A) Alum, (B) CRM conjugated GBS V, (C) CRM conjugated GBS V+trivalent vaccine (CRM conjugated GBS Ia, Ib and III), and (D) CRM conjugated GBS V+CRM conjugated GBS II trivalent vaccine (CRM conjugated GBS Ia, Ib, and III).
Figure 3B:
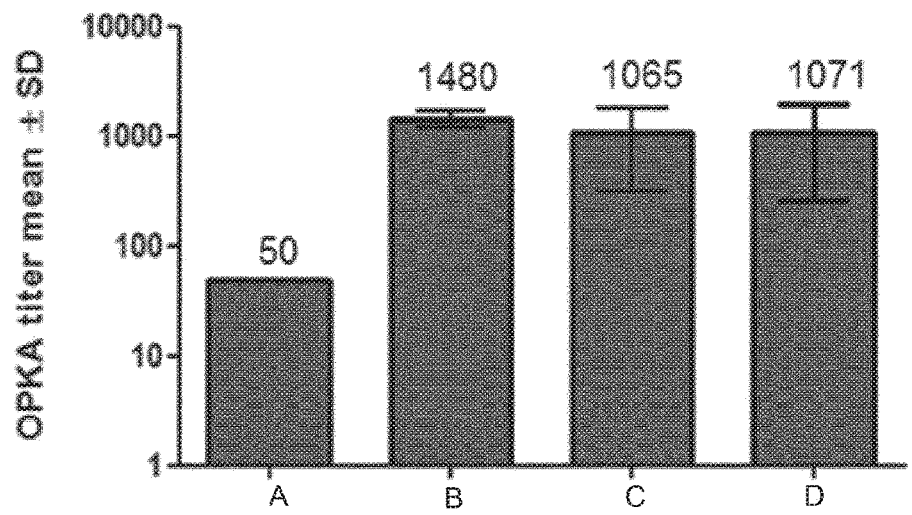

The results of these experiments are shown in FIG. 3. It can be seen that no significant immune interference was observed between CBS V and the other antigens.

The immunised mice were challenged with GBS V, and the results are provided in Table 1.

TABLE 1

Results of challenge against a GBS type V strain (type V CJB111).

| Antigens | Challenge with GBS V | |
|---|---|---|
| | Protected\Treated | % Protection |
| PBS | 39/100 | 39 |
| CRM-V | 108/119 | 91 |
| CRM-Ia/Ib/III | 32/102 | 31 |
| CRM-Ia/Ib/III + CRM-V | 60/70 | 86 |
| CRM-Ia/Ib/III + CRM-II + CRMV-V | 89/95 | 94 |

Study 3

Mice were immunised with three doses of mono- or multivalent vaccines (1 µg of each antigen) adjuvanted with aluminium salt (400 µg). The vaccines tested were (1) GBS II, (2) a tetravalent vaccine containing GBS II and the GBS trivalent vaccine, and (3) a pentavalent vaccine containing GBS II, GBV and the GBS trivalent vaccine. Mice were immunised with aluminium salt alone as a negative control. ELISA and OPK assays (using type II 5401 strain) were carried out (repeated twice).

Figure 4A:
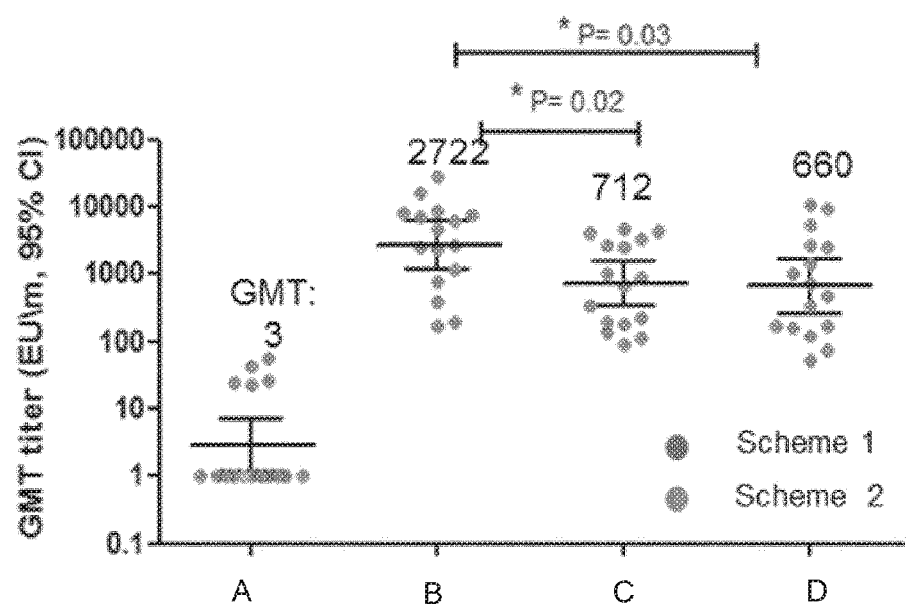
FIG. 4 shows IgG titers (FIG. 4A) and OPK titers (FIG. 4B) against GBS II. Mice were immunised with (A) Alum, (B) CRM conjugated GBS II, (C) CRM conjugated GBS II+trivalent vaccine (CRM conjugated GBS Ia, Ib and III), and (D) CRM conjugated GBS II+CRM conjugated GBS V+trivalent vaccine (CRM conjugated GBS Ia, Ib and III).
Figure 4B:
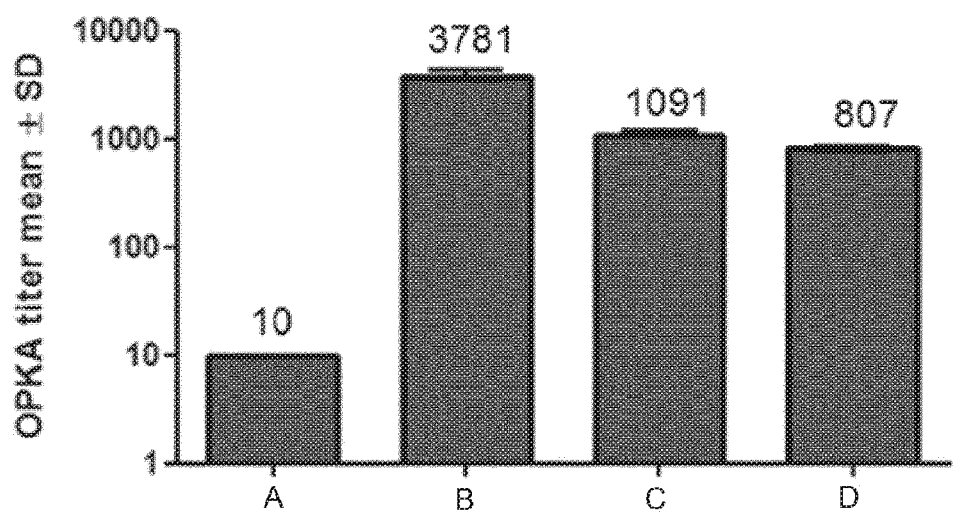

The results are shown in FIG. 4. No significant interference was observed between GBS II and the other antigens.

The immunised mice were challenged with GBS II, and the results are provided in Table 2.

TABLE 2

Results of challenge against GBS type II strain (type II 5401).

| Antigens | Challenge with GBS II | |
|---|---|---|
| | Protected\Treated | % Protection |
| PBS | 37/120 | 31 |
| CRM-II | 55/80 | 69 |
| CRM-Ia/Ib/III | 15/100 | 15 |
| CRM-Ia/Ib/III + CRM-II | 72/99 | 73 |
| CRM-Ia/Ib/III + CRM-II + CRM-V | 62/129 | 48 |

Study 4

Mice were immunised with three doses of tri- or pentavalent vaccines (1 µg of each antigen) adjuvanted with aluminium salt (400 µg). The vaccines tested were (1) GBS II, (2) the GBS trivalent vaccine (CRM197 conjugated GBS Ia, Ib and III), (3) the GBS tetravalent vaccine (CRM197 conjugated GBS Ia, Ib, II and III or CRM197 conjugated GBS Ia, Ib, and III+TT conjugated GBS II) and (4) a pentavalent vaccine containing (CRM197 conjugated GBS Ia, Ib, II, III and V or CRM197 conjugated GBS Ia, Ib, and III+TT conjugated GBS II and V). Mice were immunised with aluminium salt alone as a negative control. ELISA and OPK assays (using type II 5401 strain) were carried out (repeated twice).

The immunised mice were challenged with CBS II, and the results are provided in Table 3.

TABLE 3

Results of challenge against GBS type II strain (type II 5401).

| Antigens | Challenge with GBS II | |
|---|---|---|
| | Protected\Treated | % Protection |
| PBS | 19/60 | 31% |
| CRM-II | 23/30 | 77% |
| CRM-Ia/Ib/III | 8/30 | 26% |
| CRM-Ia/Ib/III + CRM-II | 40/50 | 80% |
| CRM-Ia/Ib/III + CRM-II + CRM-V | 32/77 | 41% |
| CRM-Ia/Ib/III + TT-II | 62/77 | 80% |
| CRM-Ia/Ib/III + TT-II + TT-V | 75/77 | 97% |

Study 5

Mice were immunised with three doses of tri- or pentavalent vaccines (1 µg of each antigen) adjuvanted with aluminium salt (400 µg). ELISA and OPK assays (using type II 5401 strain) were carried out (repeated twice).

Figure 5A:
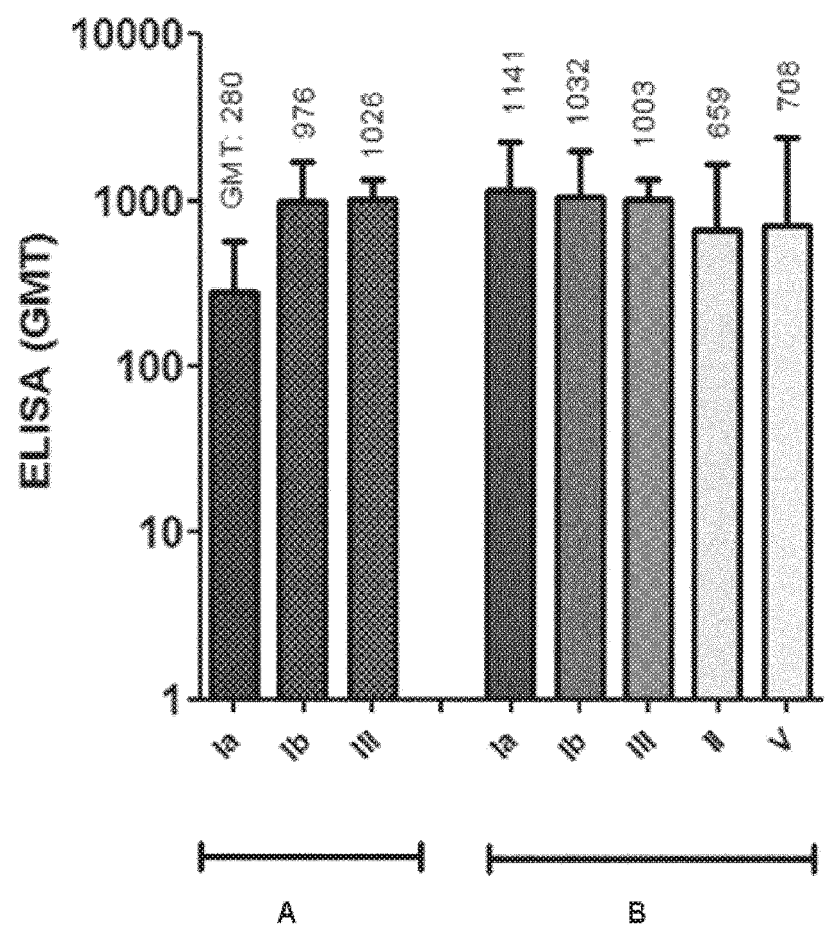
FIGS. 5A and 5B show IgG titers (5A) against GBS Ia, Ib, II, III and V and OPK titers (5B) against strains 515 Ia, H36B, COH1, 5401, CJB111. Mice were immunised with (A) trivalent vaccine: CRM conjugated GBS Ia, Ib and III and (B) pentavalent vaccine: CRM conjugated GBS Ia, Ib, II, III and V.
Figure 5B:
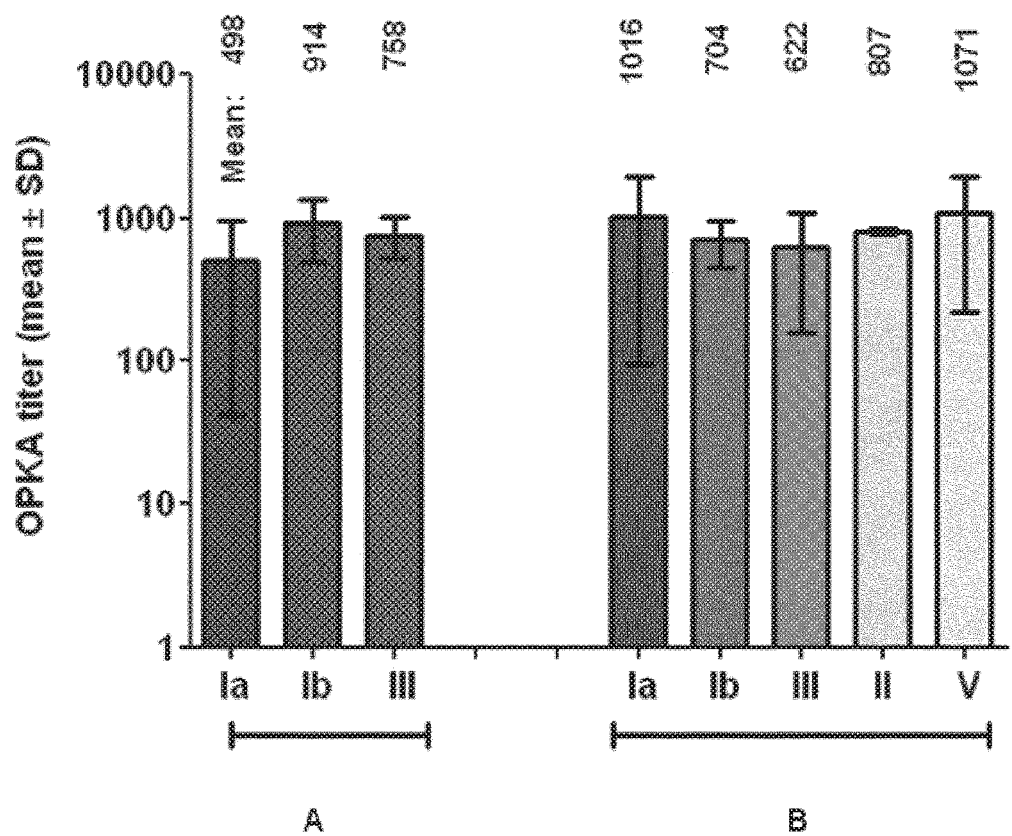

The results are shown in FIGS. 5A and 5B. No significant interference was observed between the tri- and the pentavalent vaccines.

Immunogenicity and protection of the conjugates Ia, Ib and III are not affected by the addition of PS-II and V. Comparable ELISA and OPK titers against each PS in the pentavalent formulation.

Study 6

The immunogenicity of GBS saccharides conjugated to different carrier proteins was investigated.

Figure 6:
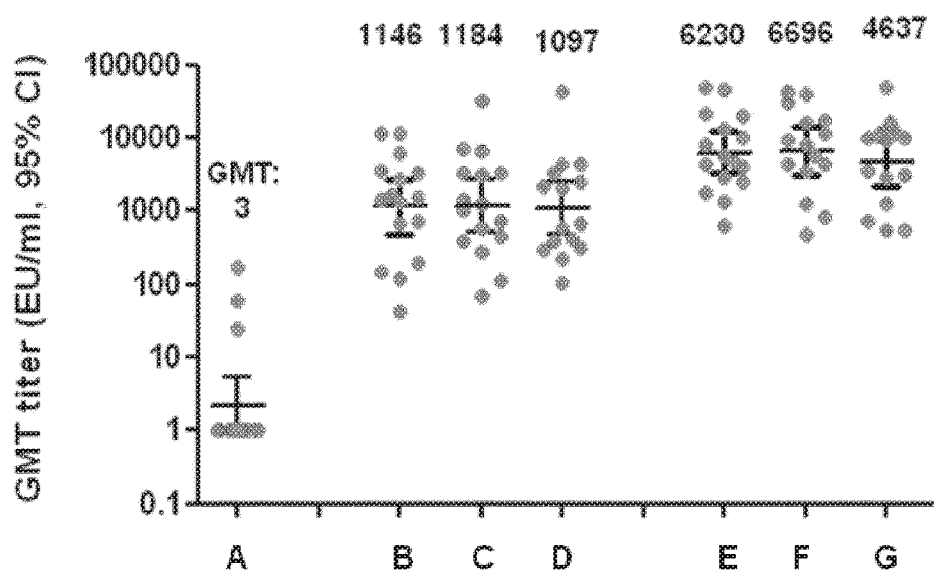
FIG. 6 shows IgG titers against GBS V. Mice were immunised with (A) PBS/Alum, (B) CRM conjugated GBS V, (C) CRM conjugated GBS V+trivalent vaccine (CRM197 conjugated GBS Ia, Ib and III), (D) CRM conjugated GBS II and V+trivalent vaccine (CRM197 conjugated Ia, Ib, III), (E) TT conjugated GBS V, (F) TT conjugated GBS V+trivalent vaccine (CRM197 conjugated GBS Ia, Ib and III), (G) TT conjugated GBS II and V+trivalent vaccine (CRM197 conjugated Ia, Ib, III).
Figure 7:
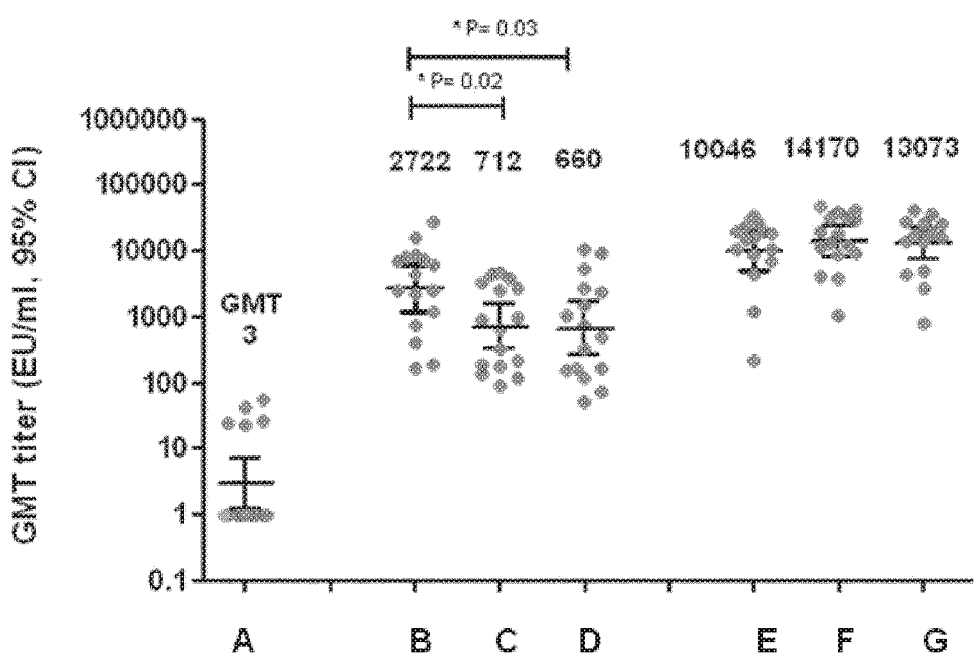
FIG. 7 shows IgG titers against GBS II. Mice were immunised with (A) PBS/Alum, (B) CRM conjugated GBS II, (C) CRM conjugated GBS II+trivalent vaccine (CRM197 conjugated GBS Ia, Ib and III), (D) CRM conjugated GBS II and V+trivalent vaccine (CRM197 conjugated Ia. Ib, III), (E) TT conjugated GBS II, (F) TT conjugated GBS II+trivalent vaccine (CRM197 conjugated GBS Ia, Ib and III), (G) TT conjugated GBS II and V+trivalent vaccine (CRM197 conjugated Ia, Ib, III).

Mice were immunized with compositions containing GBS II and/or V conjugated to CRM197 ("CRM") or tetanus toxoid ("TT"). The antibody titre against GBS V was analysed by ELISA. The results are shown in FIGS. 6 and 7. Mice were immunized with PBS/aluminium salt only as negative controls.

It can be seen that CRM and TT conjugates both provide significant immune responses against the corresponding antigen. For GBS II, no significant immune interference was observed between GBS II and the other antigens in the multivalent vaccines, irrespective of whether it is conjugated to CRM or TT. Similarly for GBS V, no significant immune interference was observed between GBS V and the other antigens in the multivalent vaccines, irrespective of whether it is conjugated to CRM or TT.

Study 7

To investigate the contribution of the sialic acid component, *Streptococcus agalactiae* capsular polysaccharide antigens Ia, Ib and II conjugated to CRM197 were tested. Vaccine lots with different sialic acid content were prepared and used to immunize mice and determine IgG titers, functional activity of induced antibodies and elicited protection against GBS in a mouse maternal immunization/neonatal challenge model. Monovalent lots of Polysaccharide-CRM197 conjugates with different sialic acid content, from 100% to <5%, were produced by treatment of native conjugates in mild acidic conditions (e.g. pH 4.75 at 80° C. for different incubation times). Potency was evaluated by IVRP. Sera from mice immunized with desialylated lots were analyzed by ELISA and Osonophagocytosis Assay (OPKA) in order to test vaccine immunogenicity and functional activity of induced antibodies, respectively. Survival experiments were also conducted to study protection in pups born to female mice receiving the vaccines.

Briefly, GBS conjugates were desialylated by treatment with deuterated sodium acetate. Sialic acid content was monitored by NMR technology. For all preparations, 3 mg of conjugate (determined by total saccharide content) were dried under vacuum (Genevac mod. EZ-2 Plus) and dissolved in 3 mL of deuterated (D2O—Aldrich 151882-100G Lot #STBC04462V) 50 mM sodium acetate at pH 4.75

(Sigma S80750-500G Lot#050M0213V); the mixture was incubated at 80° C. at different times and aliquots of the obtained preparations were characterized as follows: (1) 1H NMR analysis to estimate the ratio of bound/free sialic acid content, (2) Estimation of saccharide content based on Galactose (Gal) determination, (3) Determination of protein content, (4) SDS-PAGE analysis and (5) Capillary Electrophoresis (data not shown).

Monovalent lots of Polysaccharide-CRM197 conjugates with different SA from 100% (native untreated material) to 0% were formulated in Alum and administered to groups of 5 week-old CD1 female mice by intraperitoneal (i.p.) injection on days 1 and 21. After the second immunization on day 21, females were mated and pups were challenged with a LD90 dose of GBS of the same serotype (GBS 090 for serotype Ia, GBS H36b for Ib and GBS M781 for serotype III). Mortality was recorded daily for 3 days after challenge. Vaccine immunogenicity was tested by analyzing sera collected 2 weeks after the last vaccine injection for the presence of antibodies to each of the serotype specific antigens (Ia, Ib and III). Specific IgG antibody titers against each polysaccharide were quantified by ELISA. Functional antibody activity was evaluated on pools of sera from animals receiving the same vaccine using the opsonophagocytosis assay (OPKA) and by neonatal challenge.

Figure 8A:
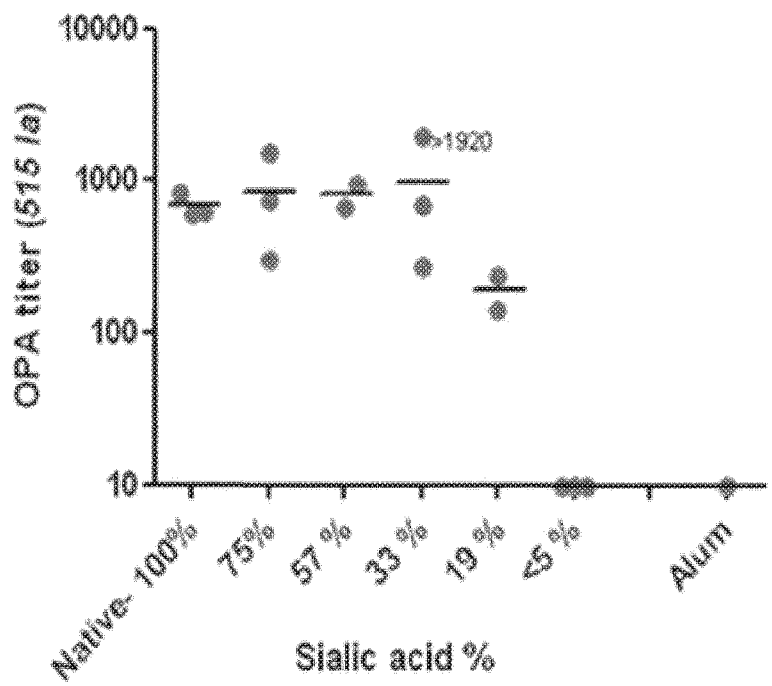
FIG. 8 shows potency analysis of samples with different sialic acid content from CRM-Ia, results from immunization with 2 doses of 1 μg of conjugates/mouse. A) OPKA titers, mean value from three protocols is represented by a horizontal bar. B): Cumulative percent survival % of challenged pups from the three protocols. C): IVRP Potency values of administered lots.
Figure 8B:
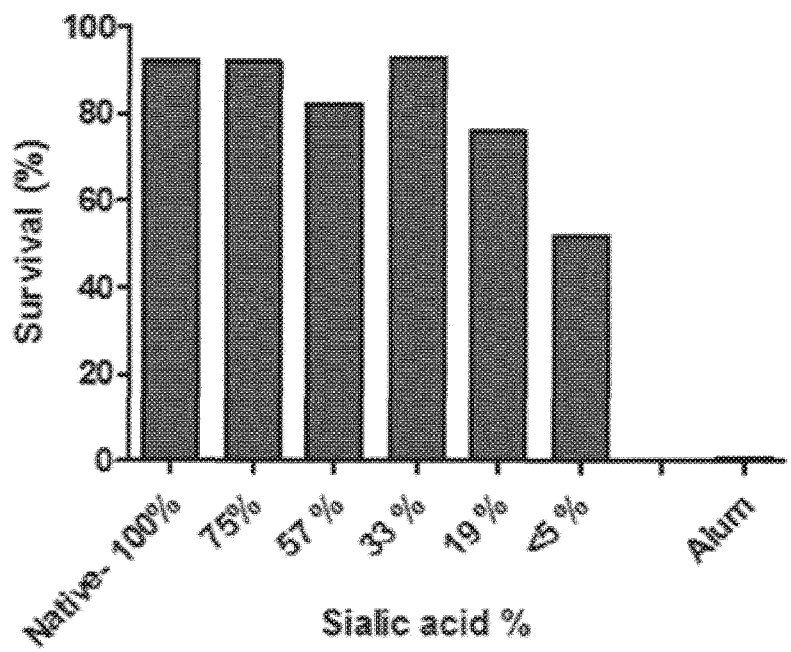
Figure 8C:
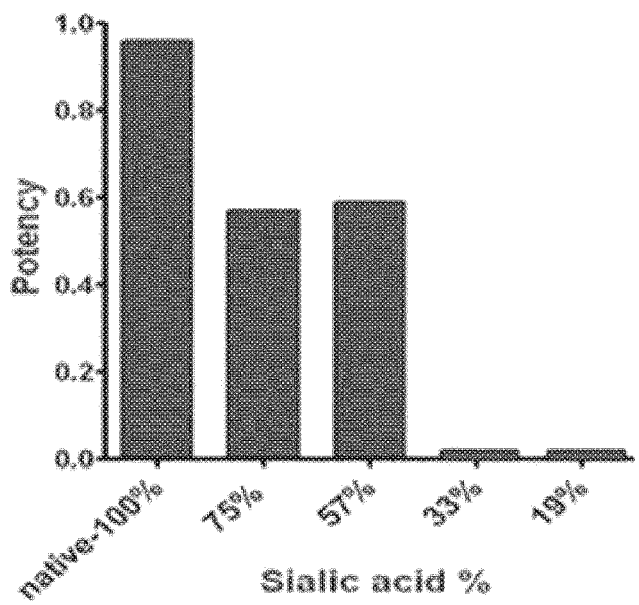

For Polysaccharide Ia-CRM197, IgG titers in animals immunized with 1 μg vaccine doses were similar for all samples except for <5%, which resulted in about 4 fold statistically significant reduction compared to native polysaccharide (P=0.0067, Mann Whitney test). A decrease in antibody functional activity could be appreciated at 19% and <5% (OPKA killing) and <5% sialic content (survival). Concerning IVRP results, potency values of samples with sialic acid content equal or below 33% decreased by more than 10 fold (FIG. 8).

Figure 9A:
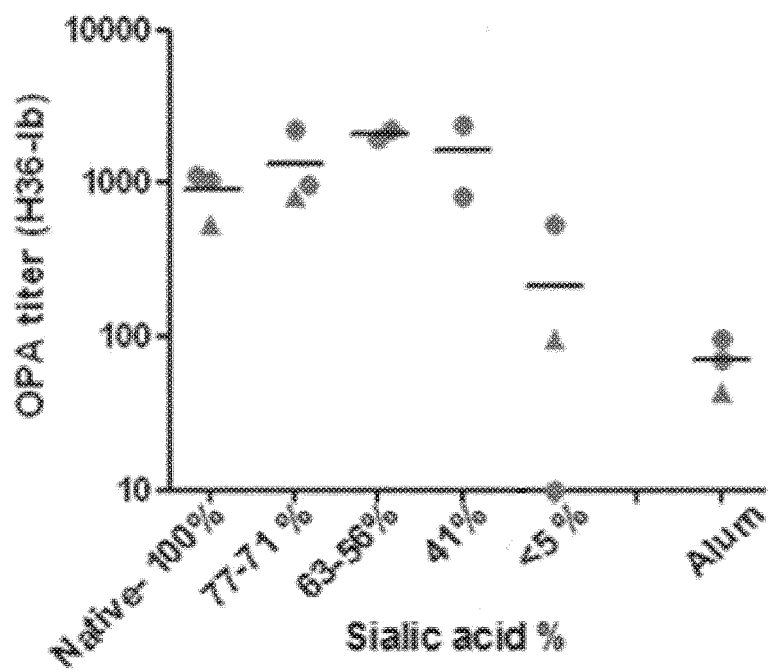
FIG. 9 shows potency analysis of desialylated CRM-Ib samples (results from immunization with 1 μg of conjugates/mouse). Panels A shows OPKA titers (pooled sera) in mice immunized with 2 doses of desialylated Ia-CRM197 samples formulated with Alum. Data from Preparation #1 are shown in triangles and from Preparation #2 are shown in circles; percent SA in the two preparations is indicated in the X axis. Horizontal bars show the mean of ELISA GMTs and OPKA titers. B): Percent survival (mean of the three protocols) of challenged pups. C) IVRP Potency values of Preparation.
Figure 9B:
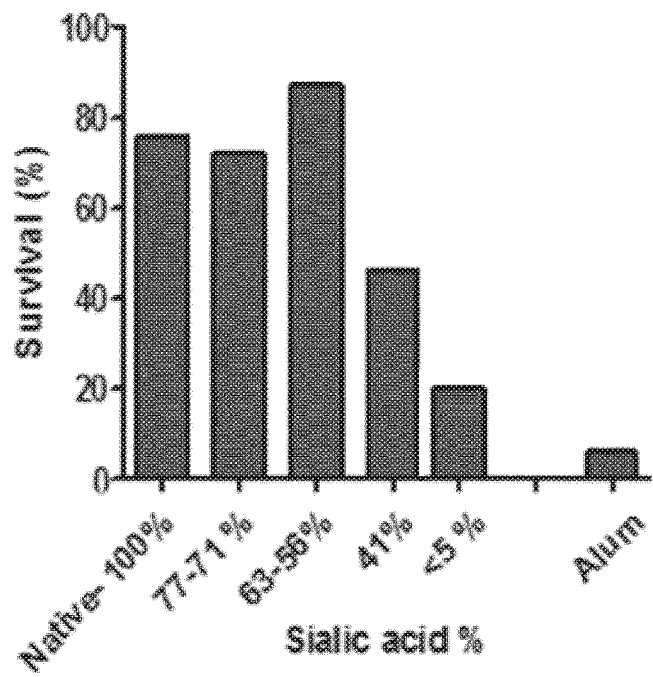
Figure 9C:
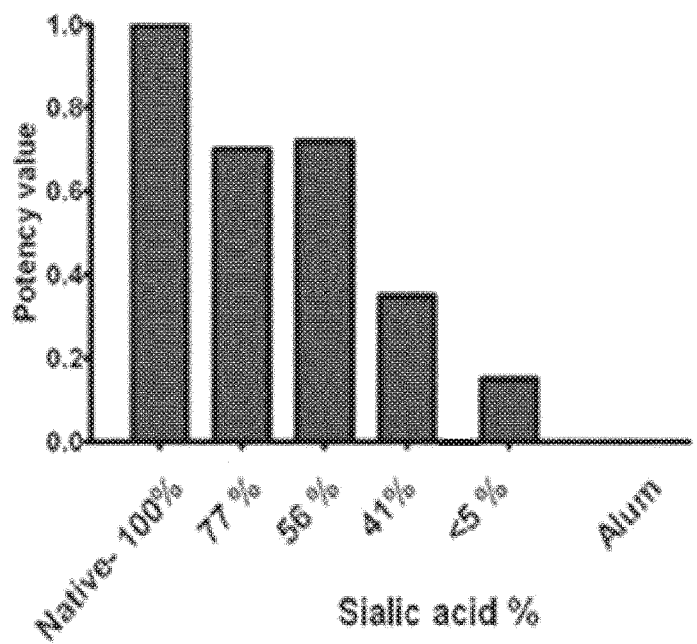

For Polysaccharide Ib-CRM197, samples containing less than 5% SA induced lower ELISA titers, OPKA titers and survival compared to samples with higher sialic content (FIG. 9).

Figure 10A:
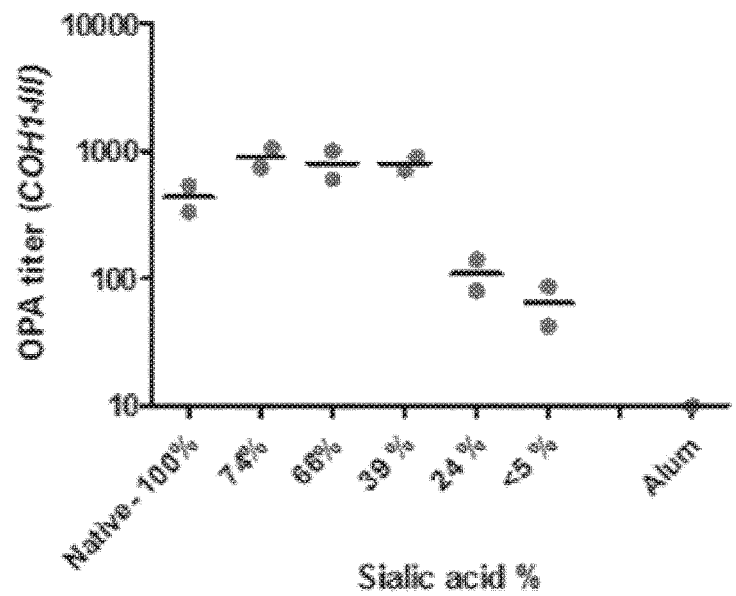
FIG. 10 shows potency analysis of desialylated CRM-III samples (results from immunization with 0.2 μg of conjugates/mouse). Panels A shows OPKA titers in sera from mice immunized with two 0.2 μg doses of Ia-CRM197 desialylated samples from Preparation #1 formulated in Alum (A) Circles represent the IgG titers from each single mouse, horizontal bars show the mean of ELISA GMTs. (b) Circles represent the OPKA titers of pooled sera from the same protocol. Panel B shows the percent survival of challenged pups from immunized female mice.
Figure 10B:
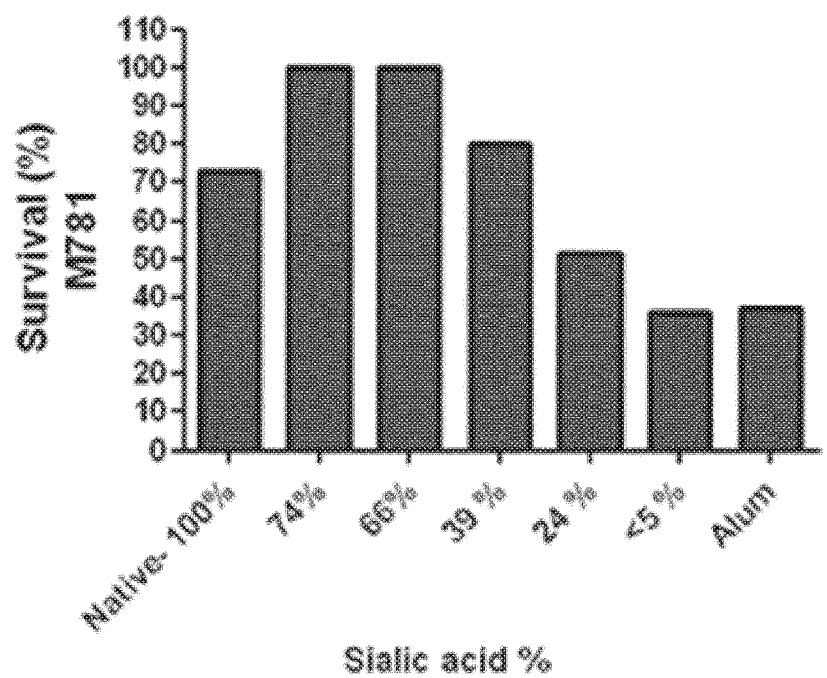

For Polysaccharide III-CRM197, IgG GMTs to PS III were significantly higher in animals who received samples containing less than 66% SA compared to those immunized with samples with higher SA content (P<0.01 Mann-Whitney test). The levels of functional antibodies were similar in animals receiving 1 μg doses of native and desialylated samples. However, a difference was appreciable in animals receiving 0.2 μg doses of conjugates, with a drastic reduction in OPKA titers in animals receiving samples with 39% SA and lower survival rates under 24% SA (FIG. 10).

Study 8

To investigate the contribution of the sialic acid component, *Streptococcus agalactiae* capsular polysaccharide antigen V conjugated to CRM197 was tested. Vaccine lots with differing sialic acid content were prepared and used to immunize mice. Monovalent lots of Polysaccharide-CRM197 conjugates with different sialic acid content, from 100% to 25%, were produced by treatment of native conjugates in mild acidic conditions (e.g. pH 4.75 at 80° C. for different incubation times).

| PSV-CRM197 Vaccine | % NeuNAc | % Protection (CJB111) |
| --- | --- | --- |
| Lot 1 + Alum | 100 | 66 |
| Lot 2 + Alum | 100 | 81 |
| Lot 3 + Alum | 100 | 69 |
| Lot 4 + Alum | 100 | 73 |
| Lot 5 + Alum | 75 | 45 |
| Lot 6 + Alum | 50 | 22 |
| Lot 7 + Alum | 50 | 36 |
| Lot 8 + Alum | 50 | 46 |
| Lot 9 + Alum | 25 | 38 |
| Lot 10 + Alum | 25 | 17 |
| Lot 11 + Alum | 25 | 10 |
| Control (Alum only) | — | 11 |
| Control 2 (Alum only) | — | 2 |

Removal of NeuNAc appears to impact protection following vaccination in mice. These experiments suggest that polysaccharide type V conjugates wherein content of NeuNAc is greater than 75% are useful.

| CRM197:PSV | % NeuNAc | % Protection (CJB111) | Crosslinking Level |
| --- | --- | --- | --- |
| 0.25:1.0 | 0 | 100 | LOW |
| 0.5:1.0 | 0 | 79 | \| |
| 0.5:1.0 | 0 | 48 | \| |
| 1.0:1.0 | 0 | 32 | \| |
| 1.0:1.0 | 0 | 46 | \| |
| 1.5:1.0 | 0 | 42 | \| |
| 1.5:1.0 | 0 | 43 | \| |
| 2.0:1.0 | 0 | 13 | \| |
| 3.0:1.0 | 0 | 37 | \| |
| 4.0:1.0 | 0 | 31 | ↓ |
| Control (Alum only) | 0 | 5 | HIGH |

The immunogenicity of Polysaccharide V-CRM197 desialated polysaccharide conjugates is inversely proportional to its cross-linking level. Thus, when an immunogenic composition comprises polysaccharide Type V, particularly desialylated polysaccharide, conjugates with lower protein:polysaccharide crosslinking levels may be beneficial.

It will be understood that the invention has been described by way of example only and modifications may be made whilst remaining within the scope and spirit of the invention.

REFERENCES

[1] Paoletti et al. (1990) *J Biol Chem* 265:18278-83.
[2] Wessels et al. (1990) *J Clin Invest* 86:1428-33.
[3] Paoletti et al. (1992) *Infect Immun* 60:4009-14.
[4] Paoletti et al. (1992) *J Clin Invest* 89:203-9.
[5] Wessels et al. (1987) *Proc Natl Acad Sci USA* 84:9170-4.
[6] Wang et al. (2003) *Vaccine* 21:1112-7.
[7] Wessels et al. (1993) *Infect Immun* 61:4760-6
[8] Wessels et al. (1995) *J Infect Dis* 171:879-84.
[9] Baker et al. (2004) *J Infect Dis* 189:1103-12.
[10] Paoletti & Kasper (2003) *Expert Opin Biol Ther* 3:975-84.
[11] WO2012/035519
[12] Lewis et al. (2004) *PNAS USA* 101:11123-8.
[13] WO2006/050341
[14] Guttormsen et al. (2008) Proc Natl Acad Sci USA. 105(15):5903-8. Epub 2008 Mar. 31.
[15] WO96/40795
[16] Michon et al. (2006) Clin Vaccine Immunol. 2006 August; 13(8):936-43.
[17] U.S. Pat. No. 6,027,733 & 6274144.
[18] www.polymer.de
[19] Wessels et al. (1989) *Infect Immun* 57:1089-94.
[20] WO2006/082527.

[21] US patent application U.S. 61/008,941, entitled "FERMENTATION PROCESSES FOR CULTIVATING STREPTOCOCCI AND PURIFICATION PROCESSES FOR OBTAINING CPS THEREFROM" filed on 20 Dec. 2007 and international patent application WO 2009/081276.
[22] Ramsay et al. (2001) *Lancet* 357(9251):195-196.
[23] Lindberg (1999) *Vaccine* 17 Suppl 2:S28-36.
[24] Buttery & Moxon (2000) *JR Coil Physicians Lond* 34:163-68.
[25] Ahmad & Chapnick (1999) *Infect Dis Clin North Am* 13:113-33, vii.
[26] Goldblatt (1998) *J. Med. Microbiol.* 47:563-7.
[27] European patent 0477508.
[28] U.S. Pat. No. 5,306,492.
[29] WO98/42721.
[30] Dick et al. in *Conjugate Vaccines* (eds. Cruse et al.) Karger, Basel, 1989, 10:48-114.
[31] Hermanson *Bioconjugae Techniques*, Academic Press, San Diego (1996) ISBN: 0123423368.
[32] U.S. Pat. No. 4,356,170.
[33] WO2006/082530.
[34] WO2005/000346.
[35] Anonymous (January 2002) *Research Disclosure*, 453077.
[36] Anderson (1983) *Infect Immun* 39(1):233-238.
[37] Anderson et al. (1985) *J Clin Invest* 76(1):52-59.
[38] EP-A-0372501.
[39] EP-A-0378881.
[40] EP-A-0427347.
[41] WO93/17712
[42] WO94/03208.
[43] WO98/58668.
[44] EP-A-0471177.
[45] WO91/01146
[46] Falugi et al. (2001) *Eur J Immunol* 31:3816-24.
[47] Baraldo et al. (2004) *Infect Immun* 72:4884-87.
[48] EP-A-0594610.
[49] WO00/56360.
[50] WO02/091998.
[51] Kuo et al. (1995) *Infect Immun* 63:2706-13.
[52] WO01/72337
[53] WO00/61761.
[54] WO00/33882
[55] WO99/42130.
[56] WO2004/011027.
[57] WO96/40242.
[58] Lei et al. (2000) *Dev Biol (Basel)* 103:259-264.
[59] WO00/38711; U.S. Pat. No. 6,146,902.
[60] International patent application PCT/IB2008/02690, 'CONJUGATE PURIFICATION', claiming priority from GB-0713880.3 (NOVARTIS AG), published as WO 2009/010877.
[61] Paoletti et al. (2001) *Vaccine* 19:2118-2126.
[62] WO00/56365.
[63] Gennaro (2000) *Remington: The Science and Practice of Pharmacy*. 20th edition. ISBN: 0683306472.
[64] Paoletti (2001) *Vaccine* 19(15-16):2118-26.
[65] WO03/009869.
[66] Almeida & Alpar (1996) *J. Drug Targeting* 3:455-467.
[67] Agarwal & Mishra (1999) *Indian J Exp Biol* 37:6-16.
[68] WO00/53221.
[69] Jakobsen et al. (2002) *Infect Immun* 70:1443-1452.
[70] Bergquist et al. (1998) *APMIS* 106:800-806.
[71] Baudner et al. (2002) *Infect Immun* 70:4785-4790.
[72] Ugozzoli et al. (2002) *J Infect Dis* 186:1358-1361.
[73] U.S. Pat. No. 6,355,271.
[74] WO00/23105.
[75] *Vaccine Design* . . . (1995) eds. Powell & Newman. ISBN: 030644867X. Plenum.
[76] WO90/14837.
[77] Podda (2001) *Vaccine* 19:2673-80.
[78] Frey et al. (2003) *Vaccine* 21:4234-7.
[79] U.S. Pat. No. 6,299,884.
[80] U.S. Pat. No. 6,451,325.
[81] U.S. Pat. No. 5,057,540.
[82] WO96/33739.
[83] EP-A-0109942.
[84] WO96/11711.
[85] WO00/07621.
[86] Barr et al. (1998) *Advanced Drug Delivery Reviews* 32:247-271.
[87] Sjolanderet et al. (1998) *Advanced Drug Delivery Reviews* 32:321-338.
[88] Niikura et al. (2002) *Virology* 293:273-280.
[89] Lenz et al. (2001) *J Immunol* 166:5346-5355.
[90] Pinto et al. (2003) *J Infect Dis* 188:327-338.
[91] Gerber et al. (2001) *Virol* 75:4752-4760.
[92] WO03/024480
[93] WO03/024481
[94] Gluck et al. (2002) *Vaccine* 20:B 10-B 16.
[95] EP-A-0689454.
[96] Johnson et al. (1999) *Bioorg Med Chem Lett* 9:2273-2278.
[97] Evans et al. (2003) *Expert Rev Vaccines* 2:219-229.
[98] Meraldi et al. (2003) *Vaccine* 21:2485-2491.
[99] Pajak et al. (2003) *Vaccine* 21:836-842.
[100] Kandimalla et al. (2003) *Nucleic Acids Research* 31:2393-2400.
[101] WO02/26757.
[102] WO99/62923.
[103] Krieg (2003) *Nature Medicine* 9:831-835.
[104] McCluskie et al. (2002) *FEMS Immunology and Medical Microbiology* 32:179-185.
[105] WO98/40100.
[106] U.S. Pat. No. 6,207,646.
[107] U.S. Pat. No. 6,239,116.
[108] U.S. Pat. No. 6,429,199.
[109] Kandimalla et al. (2003) *Biochemical Society Transactions* 31 (part 3):654-658.
[110] Blackwell et al. (2003) *J Immunol* 170:4061-4068.
[111] Krieg (2002) *Trends Immunol* 23:64-65.
[112] WO01/95935.
[113] Kandimalla et al. (2003) *BBRC* 306:948-953.
[114] Bhagat et al. (2003) *BBRC* 300:853-861.
[115] WO03/035836.
[116] WO95/17211.
[117] WO98/42375.
[118] Beignon et al. (2002) *Infect Immun* 70:3012-3019.
[119] Pizza et al. (2001) *Vaccine* 19:2534-2541.
[120] Pizza et al. (2000) *Int J Med Microbiol* 290:455-461.
[121] Scharton-Kersten et al. (2000) *Infect Inmmun* 68:5306-5313.
[122] Ryan et al. (1999) *Infjct Immun* 67:6270-6280.
[123] Partidos et al. (1999) *Immunol Lett* 67:209-216.
[124] Peppoloni et al. (2003) *Expert Rev Vaccines* 2:285-293.
[125] Pine et al. (2002) *J Control Release* 85:263-270.
[126] Domenighini et al. (1995) *Mol Micnobiol* 15:1165-1167.
[127] WO99/40936.
[128] WO99/44636.
[129] Singh et al] (2001) *J Cont Release* 70:267-276.
[130] WO99/27960.

[131] U.S. Pat. No. 6,090,406
[132] U.S. Pat. No. 5,916,588
[133] EP-A-0626169.
[134] WO99/52549.
[135] WO01/21207.
[136] WO01/21152.
[137] Andrianov et al. (1998) *Biomaterials* 19:109-115.
[138] Payne et al. (1998) *Adv Drug Delivey Review* 31:185-196.
[139] Stanley (2002) *Clin Exp Dermnatol* 27:571-577.
[140] Jones (2003) *Curr Opin Investig Drugs* 4:214-218.
[141] WO04/60308
[142] WO04/64759.
[143] WO99/11241.
[144] WO94/00153.
[145] WO98/57659.
[146] European patent applications 0835318, 0735898 and 0761231.
[147] Hennings et al. (2001) *J Infect Dis.* 183(7): 1138-42. Epub 2001 Mar. 1.
[148] Lin et al. (2001). *Inject Dis.* 184(8):1022-8.
[149] Lin et al. (2004) *J Infect Dis.* 190(5):928-34
[150] Glezen & Alpers (1999) *Clin. Infect. Dis.* 28:219-224
[151] Madoff et al. (1994) *J Clin Invest* 94:286-92.
[152] Paoletti et al. (1994) *Infect Immun* 62:3236-43.

The invention claimed is:

1. An immunogenic composition comprising:
   a) a conjugate that is a capsular saccharide from *Streptococcus agalactiae* (GBS) serotype Ia conjugated to a carrier protein;
   b) a conjugate that is a capsular saccharide from GBS serotype Ib conjugated to a carrier protein;
   c) a conjugate that is a capsular saccharide from GBS serotype III conjugated to a carrier protein;
   d) a conjugate that is a capsular saccharide from GBS serotype II conjugated to a carrier protein; and
   e) a conjugate that is a capsular saccharide from GBS serotype V conjugated to a carrier protein,
   wherein the capsular saccharide from GBS serotype V has an N-acetyl-neuraminic acid content of greater than 75% compared to the N-acetyl-neuraminic acid content of a native GBS serotype V capsular saccharide, and the capsular saccharide from GBS serotype III has an N-acetyl-neuraminic acid content of between 74% and 39% compared to the N-acetyl-neuraminic acid content of a native GBS serotype III capsular saccharide.

2. The immunogenic composition according to claim 1, wherein each GBS capsular saccharide is present at an amount from 1 to 30 µg per unit dose.

3. The immunogenic composition according to claim 2, wherein the ratio of the masses of the GBS serotype Ia, Ib, II, V and III capsular saccharides is 1:1:1:1:1.

4. The immunogenic composition according to claim 1, wherein the composition is for administration in a single dose.

5. The immunogenic composition according to claim 1, wherein the immunogenic composition does not contain an aluminium salt adjuvant.

6. The immunogenic composition according to claim 1, wherein the immunogenic composition does not contain any adjuvant.

7. The immunogenic composition according to claim 1, wherein the carrier proteins in a), b), c), d) and e) are *diphtheria* toxoid, tetanus toxoid or CRM197.

8. The immunogenic composition according to claim 7, wherein the carrier proteins in a), b), c), d) and e) are CRM197.

9. The immunogenic composition according to claim 1, wherein the capsular saccharide from GBS serotype Ia has a molecular weight (MW) in the range of 150-300 kDa; the capsular saccharide from GBS serotype Ib has a MW in the range of 150-300 kDa; the capsular saccharide from GBS serotype III has a MW in the range of 50-200 kDa; the capsular saccharide from GBS serotype II has a MW in the range of 150-300 kDa; and the capsular saccharide from GBS serotype V has a MW in the range of 150-300 kDa.

10. The immunogenic composition according to claim 1, wherein the conjugate that is a capsular saccharide from GBS serotype Ia conjugated to a carrier protein has a saccharide:protein ratio (w/w) between about 1:1 to 1:2; the conjugate that is a capsular saccharide from GBS serotype Ib conjugated to a carrier protein has a saccharide:protein ratio (w/w) between about 1:1 to 1:2; the conjugate that is a capsular saccharide from GBS serotype II conjugated to a carrier protein has a saccharide:protein ratio (w/w) between about 1:1 to 1:2; the conjugate that is a capsular saccharide from GBS serotype V conjugated to a carrier protein has a saccharide:protein ratio (w/w) between about 1:1 to 1:2; and the conjugate that is a capsular saccharide from GBS serotype III conjugated to a carrier protein has a saccharide:protein ratio (w/w) between about 3:1 to 1:1.

11. The immunogenic composition according to claim 1, wherein the composition is for administration intramuscularly.

12. The immunogenic composition according to claim 1, wherein the composition is an injectable liquid solution or suspension.

13. The immunogenic composition according to claim 1, wherein the composition is lyophilised.

14. The immunogenic composition according to claim 1, wherein the composition is a vaccine.

15. The immunogenic composition according to claim 1, wherein the composition is for administration to a human.

16. The immunogenic composition according to claim 1, wherein the composition is for administration to humans selected from females of child-bearing age, pregnant females and elderly patients.

17. The immunogenic composition according to claim 14, wherein the composition is for the prevention and/or treatment of a disease caused by *S. agalactiae*.

18. The immunogenic composition according to claim 17, wherein the disease is neonatal sepsis, bacteremia, neonatal pneumonia, neonatal meningitis, endometritis, osteomyelitis or septic arthritis.

* * * * *